US 6,413,717 B1

(12) United States Patent
Sun et al.

(10) Patent No.: US 6,413,717 B1
(45) Date of Patent: Jul. 2, 2002

(54) METHODS FOR INDENTIFYING ANTI-CANCER AGENTS

(75) Inventors: Yilong Sun, Fort Lee, NJ (US); Paul B. Fisher, Scarsdale, NY (US); Neil I. Goldstein, Maplewood, NJ (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/040,981

(22) Filed: Mar. 18, 1998

(Under 37 CFR 1.47)

(51) Int. Cl.⁷ .............................. C12Q 1/68; C12P 19/34
(52) U.S. Cl. ............................................. 435/6; 435/91.2
(58) Field of Search ..................................... 435/6, 91.2

(56) References Cited

U.S. PATENT DOCUMENTS

| | | | |
|---|---|---|---|
| 5,580,722 A | * 12/1996 | Foulkes et al. | 435/6 |
| 5,710,137 A | 1/1998 | Fisher | 514/44 |
| 5,744,300 A | * 4/1998 | Linskens et al. | 435/6 |

FOREIGN PATENT DOCUMENTS

| WO | WO 92/13091 | 8/1992 |
|---|---|---|
| WO | WO 92/16661 | 10/1992 |
| WO | WO 95/11986 | 5/1995 |

OTHER PUBLICATIONS

Amato, Science 257:330–3321, 1992.*
Tse and Forget, "Reverse Transcription and Direct Amplification of Cellular RNA Transcripts by Taq Polymerase," *Gene* 88(2):93–296, 1990.
Jiang et al., "Subtraction hybridization identifies a novel melanoma differentiation associated gene, mda–7, modulated during human melanoma differentiation, growth and progression," *Oncogene* 11: 2477–2486, 1995.

* cited by examiner

*Primary Examiner*—Eggerton A. Campbell
(74) *Attorney, Agent, or Firm*—Seed Intellectual Property Law Group PLLC

(57) ABSTRACT

Methods are provided for identifying agents that modulate the expression of genes, such as genes encoding tumor suppressor or tumor-promoting proteins. The methods generally comprise screening candidate agents for the ability to enhance expression of a tumor suppressor gene, such as mda-7, or for the ability to inhibit expression of a tumor-promoting gene within a cell. Modulating agents may be used, for example, within anti-cancer therapies.

28 Claims, 2 Drawing Sheets

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1700 base pairs
      (B) TYPE: nucleic acid
      (C) STRANDEDNESS: single (D) TOPOLOGY: linear (xi) SEQUENCE DESCRIPTION: SEQ ID NO:1:

```
CTTGCCTGCA AACCTTTACT TCTGAAATGA CTTCCACGGC TGGGACGGGA ACCTTCCACC      60
CACAGCTATG CCTCTGATTG GTGAATGGTG AAGGTGCCTG TCTAACTTTT CTGTAAAAAG     120
AACCAGCTGC CTCCAGGCAG CCAGCCCTCA AGCATCACTT ACAGGACCAG AGGGACAAGA     180
CATGACTGTG ATGAGGAGCT GCTTTCGCCA ATTTAACACC AAGAAGAATT GAGGCTGCTT     240
GGGAGGAAGG CCAGGAGGAA CACGAGACTG AGAGATGAAT TTTCAACAGA GGCTGCAAAG     300
CCTGTGGACT TTAGCCAGAC CCTTCTGCCC TCCTTTGCTG GCGACAGCCT CTCAAATGCA     360
GATGGTTGTG CTCCCTTGCC TGGGTTTTAC CCTGCTTCTC TGGAGCCAGG TATCAGGGGC     420
CCAGGGCCAA GAATTCCACT TTGGGCCCTG CCAAGTGAAG GGGGTTGTTC CCCAGAAACT     480
GTGGGAAGCC TTCTGGGCTG TGAAAGACAC TATGCAAGCT CAGGATAACA TCACGAGTGC     540
CCGGCTGCTG CAGCAGGAGG TTCTGCAGAA CGTCTCGGAT GCTGAGAGCT GTTACCTTGT     600
CCACACCCTG CTGGAGTTCT ACTTGAAAAC TGTTTTCAAA AACTACCACA ATAGAACAGT     660
TGAAGTCAGG ACTCTGAAGT CATTCTCTAC TCTGGCCAAC AACTTTGTTC TCATCGTGTC     720
ACAACTGCAA CCCAGTCAAG AAAATGAGAT GTTTTCCATC AGAGACAGTG CACACAGGCG     780
GTTTCTGCTA TTCCGGAGAG CATTCAAACA GTTGGACGTA GAAGCAGCTC TGACCAAAGC     840
CCTTGGGGAA GTGGACATTC TTCTGACCTG GATGCAGAAA TTCTACAAGC TCTGAATGTC     900
TAGACCAGGA CCTCCCTCCC CCTGGCACTG GTTTGTTCCC TGTGTCATTT CAAACAGTCT     960
CCCTTCCTAT GCTGTTCACT GGACACTTCA CGCCCTTGGC CATGGGTCCC ATTCTTGGCC    1020
CAGGATTATT GTCAAAGAAG TCATTCTTTA AGCAGCGCCA GTGACAGTCA GGGAAGGTGC    1080
CTCTGGATGC TGTGAAGAGT CTACAGAGAA GATTCTTGTA TTTATTACAA CTCTATTTAA    1140
TTAATGTCAG TATTTCAACT GAAGTTCTAT TTATTTGTGA GACTGTAAGT TACATGAAGG    1200
CAGCAGAATA TTGTGCCCCA TGCTTCTTTA CCCCTCACAA TCCTTGCCAC AGTGTGGGGC    1260
AGTGGATGGG TGCTTAGTAA GTACTTAATA AACTGTGGTG CTTTTTTTGG CCTGTCTTTG    1320
GATTGTTAAA AAACAGAGAG GGATGCTTGG ATGTAAAACT GAACTTCAGA GCATGAAAAT    1380
CACACTGTCT GCTGATATCT GCAGGGACAG AGCATTGGGG TGGGGGTAAG GTGCATCTGT    1440
TTGAAAAGTA AACGATAAAA TGTGGATTAA AGTGCCCAGC ACAAAGCAGA TCCTCAATAA    1500
ACATTTCATT TCCCACCCAC ACTCGCCAGC TCACCCCATC ATCCCTTTCC CTTGGTGCCC    1560
TCCTTTTTTT TTTATCCTAG TCATTCTTCC CTAATCTTCC ACTTGAGTGT CAAGCTGACC    1620
TTGCTGATGG TGACATTGCA CCTGGATGTA CTATCCAATC TGTGATGACA TTCCCTGCTA    1680
ATAAAAGACA ACATAACTCA                                                1700
```

(2) INFORMATION FOR SEQ ID NO:2:

(i) SEQUENCE CHARACTERISTICS:
        (A) LENGTH: 206 amino acids
        (B) TYPE: amino acid
        (C) STRANDEDNESS:
        (D) TOPOLOGY: linear (xi) SEQUENCE DESCRIPTION: SEQ ID NO:2:

```
Met Asn Phe Gln Gln Arg Leu Gln Ser Leu Trp Thr Leu Ala Arg Pro
1               5                   10                  15

Phe Cys Pro Pro Leu Leu Ala Thr Ala Ser Gln Met Gln Met Val Val
            20                  25                  30
```

```
Leu Pro Cys Leu Gly Phe Thr Leu Leu Leu Trp Ser Gln Val Ser Gly
        35                  40                  45

Ala Gln Gly Gln Glu Phe His Phe Gly Pro Cys Gln Val Lys Gly Val
        50                  55                  60

Val Pro Gln Lys Leu Trp Glu Ala Phe Trp Ala Val Lys Asp Thr Met
65                  70                  75                  80

Gln Ala Gln Asp Asn Ile Thr Ser Ala Arg Leu Leu Gln Gln Glu Val
                85                  90                  95

Leu Gln Asn Val Ser Asp Ala Glu Ser Cys Tyr Leu Val His Thr Leu
            100                 105                 110

Leu Glu Phe Tyr Leu Lys Thr Val Phe Lys Asn Tyr His Asn Arg Thr
        115                 120                 125

Val Glu Val Arg Thr Leu Lys Ser Phe Ser Thr Leu Ala Asn Asn Phe
        130                 135                 140

Val Leu Ile Val Ser Gln Leu Gln Pro Ser Gln Glu Asn Glu Met Phe
145                 150                 155                 160

Ser Ile Arg Asp Ser Ala His Arg Arg Phe Leu Leu Phe Arg Arg Ala
                165                 170                 175

Phe Lys Gln Leu Asp Val Glu Ala Ala Leu Thr Lys Ala Leu Gly Glu
            180                 185                 190

Val Asp Ile Leu Leu Thr Trp Met Gln Lys Phe Tyr Lys Leu
        195                 200                 205

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:3:

TTACAGGACC AGAGGGACAA GAC                                      23

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:4:

CAGTGAACAG CATAGGAAGG GAG                                      23

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:5:

TCATCATCTC TGCCCCCTCT GCTG                                     24

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
```

-continued

```
        (D) TOPOLOGY: linear (xi) SEQUENCE DESCRIPTION: SEQ ID NO:6:

TCTCTTCCTC TTGTGCTCTT GCTG                                                  24
```

METHODS FOR INDENTIFYING ANTI-CANCER AGENTS

TECHNICAL FIELD

The present invention relates generally to cancer therapy, and more particularly to the identification of agents that modulate the expression of genes encoding, for example, proteins with tumor suppressor or tumor promoting activity.

BACKGROUND OF THE INVENTION

Cancer is a significant health problem in the United States and throughout the world. Although advances have been made in cancer detection and treatment, no vaccine or other universally successful preventive or therapeutic method is currently available. Management of the disease currently relies on a combination of early diagnosis and aggressive treatment, which may include one or more of a variety of therapies such as surgery, radiotherapy, chemotherapy and hormone therapy. While such therapies provide benefit to many patients, a high mortality continues to be observed for many cancers.

The development of improved anti-tumor agents would facilitate cancer prevention and treatment. Currently, such agents may be identified through the use of cumbersome in vivo screens, in which the effect of an agent on tumor development in a test animal is evaluated. Such assays are slow and expensive, and are not suitable for screening large numbers of candidate agents. Other screens for anti-tumor agents involve the use of reporter genes linked to promoters of genes believed to play a role in cancer development. Such screens may be used to identify transcriptional regulators of gene expression, but the need to clone the relevant promoter increases the time required, as well as the likelihood of errors due to the removal of the promoter sequence from its endogenous chromosomal environment.

Accordingly, there is a need in the art for improved methods for identifying anti-cancer agents. The present invention fulfills this need and further provides other related advantages.

SUMMARY OF THE INVENTION

Briefly stated, the present invention provides methods for identifying agents that modulate the expression of a gene of interest. Within certain aspects, the present invention provides methods for screening an agent for the ability to modulate expression of a gene of interest, comprising the steps of: (a) contacting a cell comprising a gene of interest with a candidate agent under conditions and for a time sufficient to permit modulation of the level of mRNA transcribed from the gene of interest; (b) generating a cell lysate comprising mRNA; (c) stabilizing the mRNA; (d) generating amplified cDNA from the mRNA using polymerase chain reaction and two primers specific for the gene of interest; (e) separating the cDNA from free primers; (f) detecting an amount of the cDNA; and (g) comparing the amount of detected cDNA with an amount detected in the absence of candidate agent, and therefrom determining the ability of the candidate agent to modulate expression of the gene of interest. One or more of the primers may be covalently linked to a tag, such as biotin. Within certain specific embodiments, the gene of interest may be a tumor suppressor gene, such as gene is mda-7, or a tumor-promoting gene; the cell may be a human cancer cell, such as a melanoma cell; step (c) may comprise contacting the mRNA with a vanidyl ribonucleoside complex; and the candidate agent may be present within an aliquot of a small molecule combinatorial library.

Within further aspects, the present invention provides methods for screening an agent for the ability to modulate expression of a tumor suppressor gene, comprising the steps of: (a) contacting a human melanoma cell capable of expressing a tumor suppressor gene with an aliquot of a small molecule combinatorial library comprising a candidate agent, wherein the step of contacting is performed under conditions and for a time sufficient to permit modulation of the level of mRNA transcribed from the tumor suppressor gene; (b) generating a cell lysate comprising mRNA; (c) adding vanidyl ribonucleoside complex to the cell lysate in an amount ranging from 1 to 10 mM; (d) generating cDNA from the mRNA using polymerase chain reaction and two primers specific for the tumor suppressor gene, wherein at least one primer is covalently linked to a tag; (e) separating the cDNA from free primers; (f) detecting an amount of the tag; and (g) comparing the amount of detected tag with an amount detected in the absence of candidate agent, and therefrom determining the ability of the candidate agent to modulate expression of the tumor suppressor gene.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1A shows the levels of the control GADPH mRNA and FIG. 1B shows the levels of mda-7 mRNA.

DETAILED DESCRIPTION OF THE INVENTION

Figure 1A:
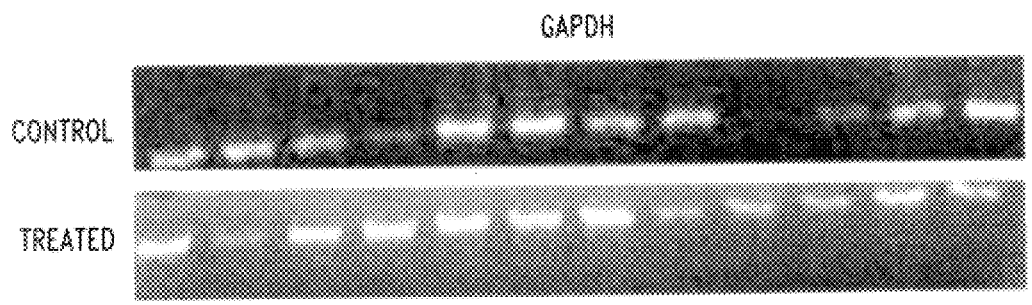
FIGS. 1A and 1B are photographs illustrating the results of a representative high-throughput screen for tumor suppressor gene expression. The expression of mda-7 in HO-1 cells, either untreated (control) or treated with beta-interferon and mezerein for 24 hours, as indicated, is shown.

As noted above, the present invention provides methods for identifying agents that modulate the expression of a gene of interest. Within certain embodiments, the gene of interest encodes a tumor suppressor or tumor-promoting protein. Accordingly, the methods provided herein may be used, for example, to identify anti-cancer agents that enhance expression of a tumor suppressor gene or that inhibit expression of a tumor promoting gene.

As used herein, an agent is said to modulate expression of a gene of interest if the level of mRNA transcribed from the gene in a cell is statistically higher or lower in the presence of the agent than in the absence of the agent. Preferably, contact of the cell with the agent, as described herein, results in at least a 5 fold increase or decrease, and more preferably at least a 10 fold increase or decrease, in the level of mRNA transcribed from the gene of interest.

The gene of interest may, within certain embodiments, be a tumor suppressor gene or a tumor promoting gene. As used herein, a "tumor suppressor" gene is a gene whose expression correlates with tumor suppressor activity (i.e., an increase in expression of the gene may induce a statistically significant decrease in tumor cell growth and/or induces apoptosis of tumor cells). Tumor suppressor genes include, but are not limited to, classical tumor suppressor genes such as p53 and p16 which are mutated or deleted in a cancer. Also included are genes such as mda-7, where overexpression of the gene in cancer cells leads to cell death by apoptosis or other mechanisms. Tumor suppressor activity of a protein may generally be evaluated using well known assays, such as an in vitro soft agar cloning assay or an in vivo tumorgenicity assay using, for example, nude mice xenografts). Tumor suppressor genes include, but are not limited to, mda-7, the sequence of which is provided in Jiang et al. *Oncogene* 11:2477–2486, 1995 and SEQ ID NOS: 1 and 2.

A "tumor-promoting" gene is a gene whose expression correlates with tumor development (i.e., an increase in expression of the gene induces a statistically significant increase in tumor cell growth). "Tumor promoting" activity may generally be assessed using any well known assay, as described above.

The methods provided herein employ cells capable of expressing the gene of interest. In other words, the cells must contain a polynucleotide comprising the sequence of the gene operably linked to a promoter and other regulatory sequences that are involved in in vivo regulation of transcription of the gene. The gene need not be detectably expressed within the cells in the absence of a modulating agent. Within certain embodiments, the cells comprise the gene of interest in an endogenous environment (i.e., the gene is not introduced into the cell by recombinant means). For example, a cancer cell may be used to identify agents that enhance the expression of an endogenous tumor suppressor gene or that inhibit the expression of an endogenous tumor-promoting gene. Suitable cancer cells include human cancer cells, such as, but not limited to, melanoma cells (e.g., HO-1 cells) and carcinoma cells derived from, for example, prostate, lung, colorectal, breast, liver and head and neck cancer (e.g., HeLa, DU-145, LnCap or A431 cells).

To screen an agent for the ability to modulate expression of the gene of interest, a cell comprising the gene is contacted with a candidate agent. Such contacting is generally performed under conditions and for a time sufficient to permit modulation of gene expression. Such conditions should allow cell survival (e.g., incubation at 37° C. in growth medium). The agent should be present in an amount ranging from 10 $\mu$M to 100 mM, and should be incubated for an amount of time that is adequate to allow a known modulating agent to affect gene expression. In general, incubation for about 12 hours (e.g., overnight) is sufficient. If desired, a substance, such as DMSO, that facilitates entry of the agent into the cell may be included in the incubation. The step of contacting may be performed in any suitable container. For high-throughput screens, the use of a 96-well microtiter plate may be convenient. Within such screens, cells may generally be added to the wells in an amount ranging from $5 \times 10^3$ to $1 \times 10^5$, preferably about $1–2 \times 10^4$, cells/well in a volume of about 100 $\mu$l.

Any of a variety of candidate agents may be employed within the methods provided herein. Within certain preferred embodiments, a small molecule combinatorial library may be screened. Such libraries are commercially available from a number of sources (or may be prepared using techniques that are well known in the art), and comprise large numbers of different small molecules, each of which may be considered a candidate agent. To screen such a library, successive dilutions are generally combined with cells in, for example, the wells of a microtiter plate. The most dilute aliquot that modulates gene expression, as described herein, may then be further diluted and tested to identify the active agent. Other candidate agents include cytokines and growth factors, as well as any other compound that may have an effect on gene expression.

In addition to incubating cells with a candidate agent, positive and negative controls may be included. For a negative control, cells are incubated under identical conditions in the absence of candidate agent (e.g., growth medium alone is added to the cells). For a positive control, an agent known to modulate gene expression may be added to the cells. For example, within embodiments in which the gene of interest is mda-7, human fibroblast interferon (IFN-$\beta$; 2000 U) and the anti-leukemic compound mezerein (MEZ; 10 ng/mL) may be used. Such compounds induce an increase in mda-7 expression, as well as an irreversible loss of proliferative potential and the induction of terminal differentiation in human melanoma cells.

After the step of contacting is complete, growth medium is generally removed, and the cells may be washed with, for example, serum-free medium. Cells are then lysed. For convenience, PCR-buffer containing 0.5% NP-40 may be used within this step, although other lysis buffers may also be employed. The lysate is then typically separated from cell debris by, for example, centrifugation followed by transfer of the supernatant to a clean container (e.g., a 96 well plate).

Prior to amplification, it is generally beneficial to stabilize the mRNA by neutralizing any RNases present within the lysate. Within the context of the present invention, mRNA should be stabilized by the addition of vanidyl ribonucleoside complex (see Sambrook et al., *Molecular Cloning: A Laboratory Manual*, Cold Spring Harbor Laboratories, Cold Spring Harbor, N.Y., 1989). This complex may generally be added to a concentration ranging from 1 mM to 10 mM, preferably to a concentration of about 5 mM.

Polymerase chain reaction (PCR) is then used to generate amplified cDNA from the mRNA transcribed from the gene of interest. Such cDNA may be generated using two separate steps (i. e., reverse transcription followed by amplification), or in a single reaction using an enzyme with a combination of polymerase and reverse transcriptase activity (e.g., the thermostable DNA polymerase TTH, available from Clontech, Palo Alto, Calif.). Primers for use in the PCR reaction may be designed based upon the sequence of the gene of interest. Within parallel reactions, primers specific for a different gene (e.g., a gene that is expected to be expressed at a constant level) may be added for comparison purposes. In general, primers are preferably 22–30 nucleotides in length, and anneal to the target sequence at temperatures of about 60° C. Calculations of annealing temperatures may generally be performed using formulas and computer programs that are known in the art.

At least one of the primers is covalently linked to a tag. As used herein, a "tag" is a compound that facilitates the subsequent detection of the attached primer, along with any nucleic acid sequences extended from the primer and hybridizing complementary sequences. One preferred tag is biotin, which allows detection based upon interaction with streptavidin. However, other tags known in the art (such as fluorescein isothiocyanate (FITC)) may also be employed. In general, a tag may be attached to a primer using well known techniques such as chemical synthesis techniques. Preferably, a tag is covalently linked at the 5' end of the primer.

PCR may be performed using well known techniques, and any of a variety of commercially available kits may be employed. Thirty rounds of amplification is generally sufficient. Suitable PCR conditions will vary according to the cDNA to be amplified, and may be readily determined by those of ordinary skill in the art. Positive controls, as described above, may be used to confirm amplification of cDNA corresponding to the gene of interest.

Following PCR, the amplified cDNA is separated from free primers. There are numerous techniques known to those of ordinary skill in the art for performing such a separation, including the use of a commercially available column (e.g., Qiaquick multiwell PCR purification column, available from Qiagen). The cDNA may then be eluted and collected in, for example, a 96 well plate.

The covalently linked tag is then detected using any suitable technique, such as an ELISA or other immunoassay. For example, cDNA with a biotin tag may be eluted into an avidin-coated 96 well plate, such that the biotin-avidin interactions immobilize the cDNA on the surface of the well. The plates may then be probed with an anti-avidin antibody, labeled with a detectable marker. For example, the detectable marker may be horse radish peroxidase, which can be detected using a suitable substrate (e.g., TMB). In such an assay, an increase in signal correlates with a decrease in the level of cDNA corresponding to the gene of interest. Accordingly, the signal intensity varies inversely with the level of mRNA transcribed from the gene of interest in the cell. By comparing the signal intensity with that of positive and negative controls, the effect of the candidate agent may be determined.

More specifically, an avidin-coated 96 well plate may be prepared by incubating with 200 ng streptavidin overnight. Once the avidin coating is completed, the remaining protein binding sites on the support are typically blocked using any suitable blocking agent known to those of ordinary skill in the art, such as dry, nonfat milk or bovine serum albumin. The immobilized avidin is then incubated with the eluted cDNA, with or without dilution, and the covalently attached biotin is allowed to bind to the avidin. In general, an appropriate contact time (ie., incubation time) is a period of time that is sufficient to permit the binding of the biotin to the avidin. Preferably, the contact time is sufficient to achieve a level of binding that is at least 95% of that achieved at equilibrium between bound and unbound biotin. Those of ordinary skill in the art will recognize that the time necessary to achieve equilibrium may be readily determined by assaying the level of binding that occurs over a period of time. At room temperature, an incubation time of about 30 minutes is generally sufficient.

Unbound cDNA may then be removed by washing the wells with an appropriate buffer. Anti-avidin antibody, linked to a detectable marker, may then be added to the solid support. Such antibodies may be prepared using well known techniques or purchased. Preferred detectable markers include enzymes (such as horseradish peroxidase), substrates, cofactors, inhibitors, dyes, radionuclides, luminescent groups and fluorescent groups. The conjugation of antibody to detectable marker may be achieved using standard methods known to those of ordinary skill in the art. Alternatively, such conjugated antibodies are commercially available.

The antibody is then incubated with the immobilized biotin-avidin complex for an amount of time sufficient to permit the detection of unbound avidin. An appropriate amount of time may generally be determined by assaying the level of binding that occurs over a period of time. Unbound antibody is then removed and bound antibody is detected using the detectable marker. The method employed for detecting the marker depends upon the nature of the marker.

For radioactive groups, scintillation counting or autoradiographic methods are generally appropriate. Spectroscopic methods may be used to detect dyes, luminescent groups and fluorescent groups. Enzyme reporter groups may generally be detected by the addition of substrate (generally for a specific period of time), followed by spectroscopic or other analysis of the reaction products. Candidate agents that results in a statistically significant increase or decrease in expression of the gene of interest are considered modulating agents, within the context of the present invention.

Other assay formats for detecting the presence of tagged cDNA may also be employed; the above format is provided solely for the purpose of illustration.

As noted above, within certain embodiments, the gene of interest is a tumor suppressor gene, such as mda-7 (SEQ ID NOS: 1 and 2). mda-7 is a universal tumor suppressor gene, which functions as a negative regulator of melanoma progression and may also function in cancers such as breast, prostate, colorectal and lung cancer. Ectopic expression of mda-7 in cancer cells of diverse origin and genotype (e.g., p53 positive and negative) induces a reduction of colony formation and growth in vitro and, in many cases, induces growth arrest and/or apoptosis in tumor cells, but not in normal cells. Agents that enhance the expression of mda-7 and/or other such tumor suppressor genes may generally function as anti-tumor agents.

An anti-tumor agent is generally administered to a patient within a pharmaceutical composition. A pharmaceutical composition comprises one or more such agents and a physiologically acceptable carrier, excipient or diluent. Pharmaceutical compositions may additionally contain a delivery system, such as biodegradable microspheres (e.g., polylactate polyglycolate) which are disclosed, for example, in U.S. Pat. Nos. 4,897,268 and 5,075,109. Pharmaceutical compositions within the scope of the present invention may further contain additional biologically active or inactive compounds.

While any suitable carrier known to those of ordinary skill in the art may be employed in the pharmaceutical compositions of this invention, the type of carrier will vary depending on the mode of administration. Compositions may be formulated for any appropriate manner of administration including, for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, a solid carrier, such as mannitol, lactose, starch, magnesium stearate, sodium saccharine, talcum, cellulose, glucose, sucrose, and magnesium carbonate, may be employed.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Pharmaceutical compositions comprising an anti-tumor agent as described herein may be administered in a manner appropriate to the disease to be treated (or prevented). The route, duration and frequency of administration will be determined by such factors as the condition of the patient, the type and severity of the patient's disease and the method of administration. Routes and frequency of administration may vary from individual to individual, and may be readily established using standard techniques. In general, the pharmaceutical compositions may be administered by injection (e.g., intracutaneous, intramuscular, intravenous or subcutaneous), intranasally (e.g., by aspiration) or orally.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active compound release. The amount of active compound contained within a sustained release formulation depends upon the site of implantation, the rate and expected duration of release and the nature of the condition to be treated or prevented.

A suitable patient for anti-cancer therapy may be any warm-blooded animal, preferably a human. A patient may or may not be afflicted with cancer, as determined by standard diagnostic methods. Accordingly, the above pharmaceutical compositions may be used to prevent the development of cancer or to treat a patient afflicted with cancer.

In general, an appropriate dosage and treatment regimen provides the active compound(s) in an amount sufficient to provide therapeutic and/or prophylactic benefit, and appropriate dosages of anti-tumor agents may generally be determined using experimental models and/or clinical trials. The use of the minimum dosage that is sufficient to provide effective therapy is generally preferred. The effect of therapy can be monitored based on clinical parameters, using assays suitable for the condition being treated or prevented, which will be familiar to those of ordinary skill in the art. Treatment with a pharmaceutical composition should lead to an improved clinical outcome (e.g., more frequent remissions, complete or partial, or longer disease-free survival) in treated patients as compared to untreated patients.

The following Example is offered by way of illustration and not by way of limitation.

EXAMPLE

Example 1

Identification of Agents that Modulate Tumor Suppressor Gene Expression

This Example illustrates the use of a representative method as described herein to screen a small molecule combinatorial library for agents that modulate mda-7 gene expression.

HO-1 human melanoma cells (American Type Culture Collection, Rockville Md.) were plated at $1-2 \times 10^4$ cells/well in a 96 well microtiter plate. A stock solution of a combinatorial library was prepared in DMSO, with a final concentration of 1 mM. Further dilutions were made in growth medium to a final concentration of 20 µM, 2 µM and 0.2 µM. 100 µl of each dilution was added to the cells, such that the final concentrations were 10 µM, 1 µM and 0.1 µM. Growth medium alone was added to the first two wells (Row A, wells 1 and 2) of each plate; as positive controls, IFN-β (2000 U) and MEZ (10 ng/ml) were added to the next two wells (Row A, wells 3 and 4).

Cells were grown overnight at 37° C. Growth medium was then removed and the cells were washed with warmed serum-free medium. The cells were lysed using PCR buffer (100 mM Tris pH 7.6; 10 mM KCl) containing 0.5% NP-40, and the plates were centrifuged to remove debris. Supernatants were transferred to a second 96 well microtiter plate.

Vanidyl ribonucleoside complex was added to a concentration of 5 mM to stabilize the mRNA, and 10 µl of each supernatant was transferred to 2 96 well PCR plates. TTH (Epicentre Technologies; 5 units) was added, along with biotinylated mda-7 (plate 1) or GAPDH (plate 2) primers. The mda-7 primers used were:

Primer 1: 5' Bio TTACAGGACCAGAGGGACAAGAC 3' (SEQ ID NO:3)

Primer 2: 5' Bio CAGTGAACAGCATAGGAAGGGAG 3' (SEQ ID NO:4).

The GAPDH primers were:

Primer 1: 5' Bio TCATCATCTCTGCCCCCTCTGCTG 3' (SEQ ID NO:5)

Primer 2: 5' Bio TCTCTTCCTCTTGTGCTCTTGCTG 3' (SEQ ID NO:6).

Thirty rounds of PCR amplification were performed, and samples were separated using Qiaquick multiwell PCR purification columns (Qiagen, Inc.), and biotinylated product was eluted and collected into avidin coated 96 well plates. Tetramethylbenzidine (TMB) was added to the wells and incubated for 5–30 minutes, and the plates were read at 450 nm.

Figure 1B:
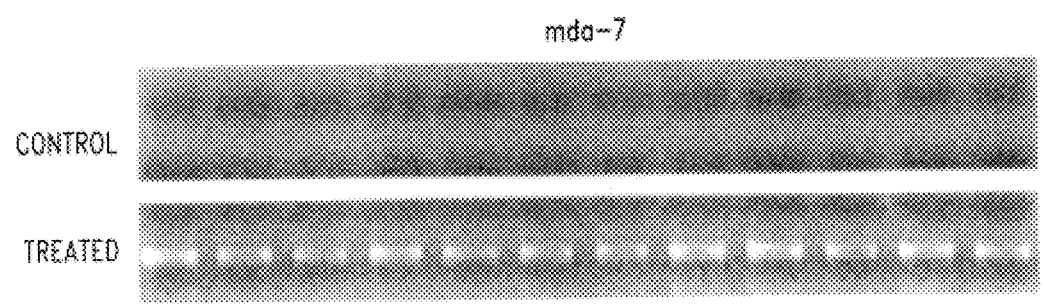
Figure 2:
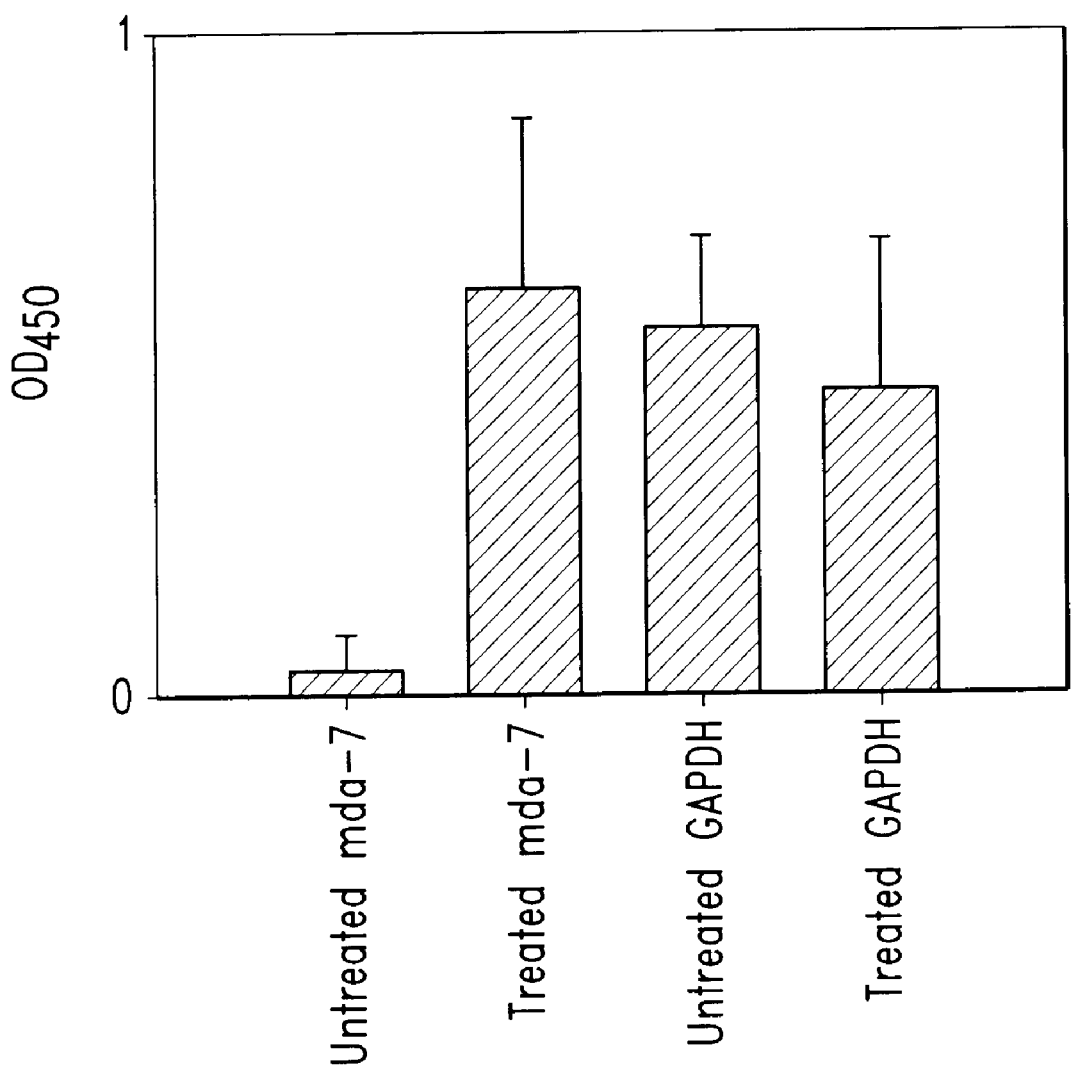
FIG. 2 is a histogram presenting the results of a representative whole cell PCR assay evaluating the expression of mda-7 in HO-1 cells, either untreated (columns 1 and 3) or treated with beta-interferon and mezerein for 24 hours (columns 2 and 4). Columns 1 and 2 show mda-7 levels, and columns 3 and 4 illustrate the levels of the control GAPDH mRNA.

FIGS. 1 and 2 present the results of the analysis performed with positive controls. mda-7 expression clearly increases in response to the treatment, whereas GAPDH expression is not induced.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for screening an agent for the ability to modulate expression of a tumor suppressor gene of interest, comprising the steps of:
   (a) contacting a cell comprising a gene of interest with a candidate agent under conditions and for a time sufficient to permit modulation of the level of mRNA transcribed from the gene of interest;
   (b) generating a cell lysate comprising mRNA;
   (c) stabilizing the mRNA;
   (d) generating amplified cDNA from the mRNA using polymerase chain reaction and two primers specific for the gene of interest;
   (e) separating the cDNA from free primers;
   (f) detecting an amount of the cDNA; and
   (g) comparing the amount of detected cDNA with an amount detected in the absence of candidate agent, and therefrom determining the ability of the candidate agent to modulate expression of the tumor suppressor gene of interest.

2. A method according to claim 1, wherein at least one of the primers is covalently linked to a tag.

3. A method according to claim 2, wherein the tag comprises biotin.

4. A method according to claim 1, wherein the tumor suppressor gene is mda-7.

5. A method according to claim 1, wherein the cell is a human cancer cell.

6. A method according to claim 5, wherein the cell is selected from the group consisting of human melanoma cells and human carcinoma cells.

7. A method according to claim 1, wherein step (c) comprises contacting the mRNA with a vanadyl ribonucleoside complex.

8. A method according to claim 1, wherein the candidate agent is present within an aliquot of a small molecule combinatorial library.

9. A method for screening an agent for the ability to modulate expression of a tumor suppressor gene, comprising the steps of:
   (a) contacting a human melanoma cell capable of expressing a tumor suppressor gene with an aliquot of a small molecule combinatorial library comprising a candidate agent, wherein the step of contacting is performed under conditions and for a time sufficient to permit modulation of the level of mRNA transcribed from the tumor suppressor gene;
   (b) generating a cell lysate comprising mRNA;
   (c) adding vanadyl ribonucleoside complex to the cell lysate in an amount ranging from 1 mM to 10 mM;
   (d) generating cDNA from the mRNA using polymerase chain reaction and two primers specific for the tumor suppressor gene, wherein at least one primer is covalently linked to a tag;
   (e) separating the cDNA from free primers;
   (f) detecting an amount of the tag; and
   (g) comparing the amount of detected tag with an amount detected in the absence of candidate agent, and therefrom determining the ability of the candidate agent to modulate expression of the tumor suppressor gene.

10. A method according to claim 9, wherein the amount of vanadyl ribonucleoside complex added to the cell lysate is about 5 mM.

11. A method for screening an agent for the ability to modulate expression of a gene of interest, comprising the steps of:
   (a) contacting a cell comprising a gene of interest with a candidate agent under conditions and for a time sufficient to permit modulation of the level of mRNA transcribed from the gene of interest;
   (b) generating a cell lysate comprising mRNA;
   (c) contacting the mRNA with a vanadyl ribonucleoside complex;
   (d) generating amplified cDNA from the mRNA using polymerase chain reaction and two primers specific for the gene of interest;
   (e) separating the cDNA from free primers;
   (f) detecting an amount of the cDNA; and
   (g) comparing the amount of detected cDNA with an amount detected in the absence of candidate agent, and therefrom determining the ability of the candidate agent to modulate expression of the gene of interest.

12. A method according to claim 11, wherein at least one of the primers is covalently linked to a tag.

13. A method according to claim 12, wherein the tag comprises biotin.

14. A method according to claim 11, wherein the gene of interest is a tumor suppressor gene.

15. A method according to claim 14, wherein the tumor suppressor gene is mda-7.

16. A method according to claim 11, wherein the gene of interest is a tumor-promoting gene.

17. A method according to claim 11, wherein the cell is a human cancer cell.

18. A method according to claim 17, wherein the cell is selected from the group consisting of human melanoma cells and human carcinoma cells.

19. A method according to claim 11, wherein the candidate agent is present within an aliquot of a small molecule combinatorial library.

20. A method for screening an agent for the ability to modulate expression of a gene of interest, comprising the steps of:
   (a) contacting a cell comprising a gene of interest with a candidate agent under conditions and for a time sufficient to permit modulation of the level of mRNA transcribed from the gene of interest;
   (b) generating a cell lysate comprising mRNA;
   (c) stabilizing the mRNA;
   (d) generating amplified cDNA from the mRNA using polymerase chain reaction and two primers specific for the gene of interest, wherein at least one of the primers is covalently linked to a tag;
   (e) separating the cDNA from free primers;
   (f) detecting an amount of the cDNA by assaying for the presence of the tag; and (g) comparing the amount of detected cDNA with an amount detected in the absence of candidate agent, and therefrom determining the ability of the candidate agent to modulate expression of the gene of interest.

21. A method according to claim 20, wherein the tag comprises biotin.

22. A method according to claim 20, wherein the gene of interest is a tumor suppressor gene.

23. A method according to claim 22, wherein the tumor suppressor gene is mda-7.

24. A method according to claim 20, wherein the gene of interest is a tumor-promoting gene.

25. A method according to claim 20, wherein the cell is a human cancer cell.

26. A method according to claim 25, wherein the cell is selected from the group consisting of human melanoma cells and human carcinoma cells.

27. A method according to claim 20, wherein step (c) comprises contacting the mRNA with a vanadyl ribonucleoside complex.

28. A method according to claim 1, wherein the candidate agent is present within an aliquot of a small molecule combinatorial library.

* * * * *